(12) United States Patent
Leblond et al.

(10) Patent No.: US 7,128,931 B2
(45) Date of Patent: Oct. 31, 2006

(54) SEMI-PERMEABLE MICROCAPSULE WITH COVALENTLY LINKED LAYERS AND METHOD FOR PRODUCING SAME

(75) Inventors: Francois Leblond, 66, rue du Vieux Moulin, Le Gardeur, Quebec (CA) J5Z 2K4; Jean-Pierre Halle, 258, Des Prairies, Laval, Quebec (CA) H7N 2T9

(73) Assignees: Francois Leblond, Quebec (CA); Jean-Pierre Halle', Quebec (CA)

( * ) Notice: Subject to any disclaimer, the term of this patent is extended or adjusted under 35 U.S.C. 154(b) by 146 days.

(21) Appl. No.: 10/686,789

(22) Filed: Oct. 17, 2003

(65) Prior Publication Data

US 2005/0147594 A1 Jul. 7, 2005

(51) Int. Cl.
*A61K 9/50* (2006.01)
(52) U.S. Cl. ...................... 424/490; 435/182
(58) Field of Classification Search ............... None
See application file for complete search history.

(56) References Cited

U.S. PATENT DOCUMENTS 5,801,033 A * 9/1998 Hubbell et al. ............. 435/182
5,827,707 A * 10/1998 Lamberti .................... 435/178

OTHER PUBLICATIONS

GH3- rat pituitary tumor cells. Technical literature from Ambion. see online at website: www.ambion.com/techlib/spec/sp_7930.pdf. entire document, reference therein.*
Pierce Biotechnology, Inc., P.O. Box 117, Rockford, IL 61105. (2002), Photoreactive crosslinkers, Technical literature, Doc. No. 0635 (for ANB-NOS, SANPAH, and Sulfo-SANPAH) and references therein. (Online- http://www.piercenet.com). Entire document.*
Zekorn TD. et al. 1996, Biocompatibility and immunology in the encapsulation of islets of Langerhans (bioartificial pancreas). Int. J. Artif. Organs, 1996 19(4): 251-257. Entire document.*
Inveradi L et al. "Islet transplantation: Immunological perspectives". Current Opinion in Immunology, 2003, 15: 507-511. entire document.*
Bank H. L., "*Assessment of Islet Cell Viability Using Fluorescent Dyes*", Diabetologia 1987; 30, p. 812-816.
Bank H. L., "*Rapid Assessment of Islet Viability with Acridine Orange and Propidium Iodine*", in Vitro Cell Dev Biol, 1988; 24, p. 266-273.

Brissova M. et al., "*Evaluation of Microcapsule Permeability via Inverse Size Exclusion Chromatography*", Anal Biochem, 1966; 242, p. 104-111.
Chang S. J. et al., "*Biocompatible Microcapsules with Enhanced Mechanical Strength*", J Biomed Mater Res. 2002; 59(1): p. 118-126.
Fritschy W. M. et al., "*Effect of Alginate-Polylysine-Alginate Microencapsulation on in Vitro Insulin Release From Rat Pancreatic Islets*", Diabetes, 1991; 40(1); p. 37-43.
Iiieva A. et al., "*Pancreatic Islet Cell Survival Following Islet Isolation: The Role of Cellular Interactions in the Pancreas*", J Endocrinol, 1999; 161, p. 357-364.
Lacy P. E. et al., "*Method for the Isolation of Intact Islets of Langerhans From the Rat Pancreas*", Diabetes, 1967; 16, p. 35-39.
Leblond F. A. et al., "*Quantitative Method for the Evaluation of Biomicrocapsule Resistance to Mechanical Stress*", Biomaterials, 1996; 17, p. 2097-2102.
Lu M. Z. et al., "*Cell Encapsulation with Alginate and Alpha-Phenoxycinnamylidene-Acetylated Poly(Allylamine)*", Biotechnol Bioeng, 2000, 70(5): p. 479-483.
Robitaille R. et al., "*Studies on Small (<350μM) Alginate-Poly-L-Lysine Microcapsules V. Determination of Carbohydrate and Protein Permeation Through Microcapsules by Reverse Size Exclusion Chromatography*", J Biomed Mater Res. 2000, 50 p. 420-427.
Seglen P.O., "*Preparation of Isolated Rat Liver Cells*", Methods Cell Biol, 1976; 13, p. 29-83.
Steward W. W. et al., "*Characterization of Calcium Alginate Pore Diameter by Size-Exclusion Chromatography Using Protein Standards*", Enzyme Microbiology & Technology, 1993; 15, p. 922-927.

* cited by examiner

*Primary Examiner*—Sandra E. Saucier
*Assistant Examiner*—Satyendra K. Singh
(74) *Attorney, Agent, or Firm*—Marc S. Kaufman; Carlos R. Villamar; Nixon Peabody, LLP

(57) ABSTRACT

The present invention relates to semi-permeable microcapsules, which exhibit an increased resistance to mechanical stresses as well as an increased resistance to chemical degradation. More specifically, this semi-permeable microcapsule has a bead enclosing a material such as living cells, covalently linked to a semi-permeable layer, made of a polycation cross-linking derivative, covering the bead. The present invention is also directed to a pharmaceutical composition comprising the above-mentioned semi-permeable microcapsules. The present invention is also directed to the use of such microcapsule in a method for microencapsulating a beaded material and in a method for treating diabetes in a subject.

33 Claims, 11 Drawing Sheets

FIG 1A: sulfosuccinimidyl 6-(4'-azido-2'-nitrophenylamino) hexanoate

FIG 1B: N-5-azido-2-nitrobenzoyloxysuccinimide

SEMI-PERMEABLE MICROCAPSULE WITH COVALENTLY LINKED LAYERS AND METHOD FOR PRODUCING SAME

FIELD OF THE INVENTION

The present invention generally relates to the field of microcapsules and more specifically to the field of semi-permeable microcapsules with covalently linked layers.

BACKGROUND OF THE INVENTION

Microencapsulation of cells in semi-permeable membranes has been proposed to prevent their immune destruction following transplantation, thus alleviating the need to use toxic immunosuppressive drugs. This approach can be used for replacing defective organs, such as insulin-producing cells for the treatment of diabetes, and for delivering natural or synthetic therapeutic molecules for the treatment of numerous diseases.

The field of microencapsulation has been faced with a number of issues hindering proper use in physiological conditions. One such issue is the resistance of microcapsules to both chemical and mechanical degradation. More precisely, microcapsules resistant to both chemical and mechanical degradation are crucial in situations wherein microcapsule delivery has to lead to highly efficient and durable treatments.

Strong microcapsules will obviously increase the durability of the transplant. It is also likely to improve long term biocompatibility of microcapsules, since a strong pericapsular reaction always develops around broken or damaged capsules. Microcapsules that can hardly be destroyed in conditions compatible with life would improve the safety of a number of different transplanted cells such as virus-transfected bioengineered cells, immortalized cells or stem cell-derived cells.

Efforts have been made to improve microcapsule strength. Of particular interest is the formation of complexes between negatively charged polyanions such as alginate and positively-charged polycations such as poly-L-lysine (PLL) to form alginate-poly-L-lysine-alginate (APA) microcapsules. This is the most widely used method to microencapsulate cells. However, one of the major drawbacks of the presently used microcapsules is their limited resistance as well as their limited membrane stability.

In order to improve microcapsule strength, the applicants, as well as others, have evaluated the effect on microcapsule strength of modulating intrinsic parameters such as PLL molecular weight, concentration and incubation time and the manuronic acid/guluronic acid ratio of alginate. The formation of neutral capsules by the introduction of a new coating agent has also been investigated. Following these experiments, electrostatic binding between PLL and alginate has been obtained. Nevertheless, poly-L-lysine still competed with other positively charged molecules present in the environment to bind to the alginate beads. A prolonged incubation in solutions with high concentrations of calcium, for example, has shown a displacement of the alginate-poly-L-lysine bonds. In addition, it has been observed that the external sheet of alginate was progressively lost from microcapsules within days or weeks.

To prevent this competition with charged molecules in the environment, a new concept is proposed: the introduction of covalent links into the membrane of the microcapsule. Covalent links are known to be more stable than electrostatic interactions. The challenge is that most methods to create or break a covalent link are incompatible with cell survival.

Introducing covalent links within the structure of the alginate layer has increased the stability of alginate beads. However, for microcapsules comprised of an alginate bead core subsequently coated, the covalent links would only solidify the inside of the microcapsules with no effect on the stability of the semi-permeable membrane or of the outer coats.

In 2001, the Wang group has also suggested a way to create covalent links but this time, within a semi-permeable layer, made of modified poly(allylamine), which plays a role similar to the one played by poly-L-lysine in alginate poly-L-lysine microcapsules (Chang, S. J., et al., *Biocompatible microcapsules with enhanced mechanical strength*. J Biomed Mater Res 59(1): p. 118–126, 2002; Lu, M. Z., et al., *A novel cell encapsulation method using photosensitive poly(allylamine) alpha-cyanocinnamylideneacetate*. J Microencapsul 17(2): p. 245–251, 2000; and Lu, M. Z., et al., *Cell encapsulation with alginate and alpha-phenoxycinnamylidene-acetylated poly(allylamine)*. Biotechnol Bioeng 70(5): p. 479–483, 2000. To enhance the microcapsule's resistance, Wang et al. proposed to graft a photodimerizable reactive group on the polycationic polymer forming the semi-permeable membrane of microcapsules. This functional reactive group has the particularity to dimerize when exposed to light allowing these cationic polymers to form covalent bonds between one another. However, the remaining problem was that the microcapsule layers were linked to one another by only weak electrostatic bonds.

While the microcapsules known in the art have resulted in the expansion of the present field, there is still a need for a new semi-permeable microcapsule, such as one that exhibits an increased resistance to mechanical stresses as well as an increased resistance to chemical degradation, while permanently preserving a defined molecular cut-off of the semi-permeable membrane.

SUMMARY OF THE INVENTION

An object of the present invention is to provide semi-permeable microcapsules, which satisfy the above-mentioned need. Accordingly, the present invention relates to semi-permeable microcapsules and the method for producing same.

According to a first aspect, the invention is directed to a semi-permeable microcapsule comprising:
  a bead suited to enclose a material; and
  a semi-permeable layer covering the bead, said semi-permeable layer being made of a polycation cross-linking derivative covalently linked to the bead.

In another aspect, the invention is directed to a method for microencapsulating a beaded material. The method comprises the steps of:
  a) providing a material enclosed within a bead to obtain a beaded material;
  b) covering the beaded material with a semi-permeable layer made of a polycation cross-linking derivative, to obtain a product; and
  c) covalently linking the beaded material to the semi-permeable layer.

In a further aspect, the present invention is directed to a pharmaceutical composition comprising a pharmaceutically acceptable carrier and a plurality of the above-mentioned semi-permeable microcapsules, each one of said microcapsules enclosing a material.

In yet another aspect, the present invention is directed to a method for treating diabetes in a subject. The method comprises the step of administering to said subject, an effective amount of the above-mentioned pharmaceutical composition.

The invention and its advantages will be better understood upon reading the following non-restrictive description of preferred embodiments thereof, made with references to the accompanying drawings.

DETAILED DESCRIPTION OF THE INVENTION

Figure 1:
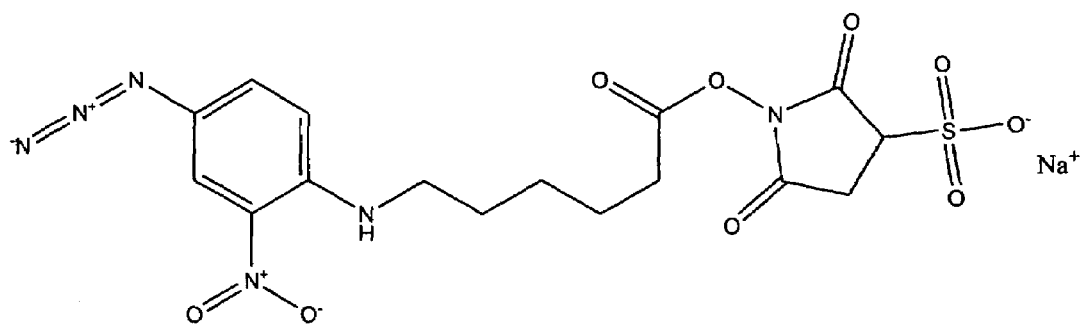
FIG. 1A shows the chemical structure of Sulfosuccinimidyl 6-(4'-azido-2'-nitrophenylamino) hexanoate (Sulfo-SANPAH).
FIG. 1B shows the chemical structure of ANB-NOS.
Figure 1:
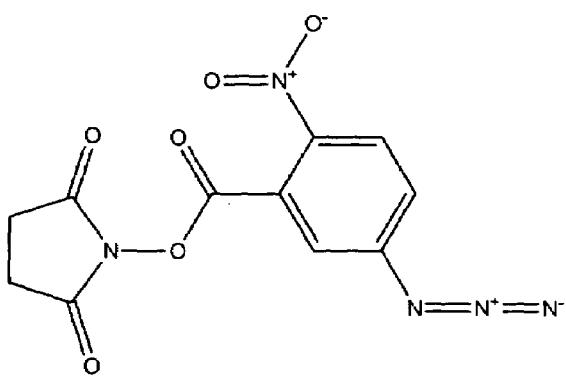

The originality of the present invention resides in that it discloses new semi-permeable microcapsules which exhibit an increased resistance to mechanical stresses as well as an increased resistance to chemical degradation, in comparison with microcapsules known in the art. In other words, the microcapsules' increased resistance leads to their stability in conditions compatible with life. In addition, these semi-permeable microcapsules have a well defined and permanent membrane molecular weight cut-off.

A) Microcapsule and Composition

According to the first aspect, the present invention relates to a semi-permeable microcapsule. More specifically, the microcapsule of the present invention comprises a bead suited to enclose a material. It will be understood that, in the context of the present invention, the term "bead" as used herein refers to a gel core, in which a material can be embedded. Such a material-containing core or bead may be formed into droplets using any suitable method as is known in the art, including but not limited to emulsification and extrusion from a needle. When using the said extrusion methods, the size of beads may be decreased and controlled with, but not limited to, an electrostatic pulse system or an air jet impinging upon the needle.

As used herein, the term "material" refers to a biological or a chemical material. For instance, such a material can be any one of the following : proteins or polypeptides; DNA or RNA polynucleotides; vectors such as plasmids; hybridoma; bacteria such as probiotic bacteria; living cells such as insulin-producing cells, preferably insulin-producing cells comprised in islets of Langherans; and any drug suitable to be enclosed in the microcapsule of the present invention.

The microcapsule of the invention also comprises a semi-permeable layer made of a polycation cross-linking derivative covalently linked to the bead, so that the semi-permeable layer covers or surrounds the bead. It will be understood that the expression "semi-permeable layer" as used herein refers to a layer that allows passage of some molecules and impedes passage of others. For instance, the contemplated semi-permeable layer of the present invention contributes, by "allowing the passage of molecules", to the diffusion of nutrients and oxygen from the environment into the vicinity of the above-described bead. It can be appreciated that such a characteristic for example, would be important for the survival of living cells which can be enclosed within said beads. In parallel, the semi-permeable layer can also impede entry of noxious or undesirable elements such as antibodies and immune cells. In this connection and according to a preferred embodiment, the semi-permeable layer contemplated by the present invention allows passage of molecules with a defined viscosity radius, such as a viscosity radius equal or inferior to about 2.7 nm. By "about", it is meant that the value of said radius can vary within a certain range depending on the margin of error of the method used to evaluate such radius and because the size of the pores of the microcapsule membrane vary within a certain range.

The expression "polycation cross-linking derivative" as used herein, refers to a compound resulting from the reaction between a polycation as described herein below and a photoactivatable cross-linking agent. The reaction between the polycation and the photoactivatable agent of the present invention preferably results in a covalent ester link between said polycation and photoactivatable agent.

The "photoactivatable cross-linking agent" contemplated by the present invention present at least the two following functional groups, namely a carboxylic acid derivative, such as a N-hydroxysuccinimide ester group at one end, and a photoreactive group, such as a phenyl azide group at the other end. It will be understood that the carboxylic acid derivative is meant to react rapidly and specifically with primary amines, such as the ones present in the above-mentioned polycation.

It will also be understood that the photoreactive group contemplated by the present invention is activated at a wavelength which will be substantially unharmful for the material enclosed in the above-mentioned beads. By the expression "substantially unharmful", it is meant that the material enclosed within the beads of the present invention will substantially retain its initial biological and physiological characteristics, even after being microencapsulated. Moreover, the photoreactive group contemplated by the present invention will be activated at a preferred wavelength of about between 320 and 350 nm. Such a wavelength corresponds to UVA light rays.

According to a preferred embodiment of the present invention, the photoactivatable cross-linking agent is N-5-Azido-2-nitrobenzoyloxysuccinimide (ANB-NOS). According to yet another preferred embodiment of the present invention, the polycation is poly-L-lysine and the photoactivatable cross-linking agent is ANB-NOS. These two components can be present at various ratios, although preferably at a 1:20 ratio.

The term "polycation" as used herein, refers to a positively-charged polymer which presents a primary amine, such as lysine or any other primary amine, as a functional group. Therefore, at physiological pH, such a polycation will display a positive net charge. More particularly, the polycation molecules present a high affinity with manuronic acid, as found in the negatively-charged compounds contemplated by the present invention. Moreover, this polycation can be of any molecular weight varying from 15 to 300 kDa, preferably varying from 18 to 30 kDa. According to a preferred embodiment, the polycation can be chitosan, synthetic polymers such as poly(allylamine) and poly(ethylenimine), or more preferably poly-L-lysine.

According to a preferred embodiment, the invention also relates to a multi-layered microcapsule. In this connection, the microcapsule of the invention preferably further comprises a biocompatible layer covalently linked to the polycation cross-linking derivative of the semi-permeable layer, so that the biocompatible layer covers or surrounds said semi-permeable layer. By "biocompatible layer", it is meant that the layer is not detrimental to the embedded material. Furthermore, the layer is considered biocompatible if it produces a minimal or no adverse response in a subject. For instance, the layer is considered "biocompatible" if there is minimal cellular growth on its surface subsequent to implantation, minimal inflammatory reaction, and no evidence of anaphylaxis during use. Thus, the layer should elicit neither a specific humoral or cellular immune response nor a nonspecific foreign body response. To determine whether the layer is biocompatible, it may be necessary to conduct specific tests, which are well known to one skilled in the art.

According to a preferred embodiment, the biocompatible layer, as well as the bead contemplated by the present invention comprises a negatively-charged compound. More preferably, both the bead and the biocompatible layer are made of the same negatively-charged compound. As used herein, the expression "negatively-charged compound" means any compound presenting negative charges thus having the potential of being electrostatically attracted to any surrounding positively-charged compound. More specifically, the only important requirement is that such negatively-charged compound, to be used for the bead or the biocompatible layer, comprises carbon-carbon or carbon-hydrogen bonds, for reacting with the photoactivatable cross-linking agent of the present invention, such as the ANB-NOS. For instance, the negatively-charged compounds contemplated by the present invention can be components of the extracellular matrix, such as heparin, or any hydrogel.

By "hydrogel" is meant any compound forming, to various degrees, a jelly-like product when suspended in a solvent, typically water or polar solvent. More specifically, such a gel can be a polymeric compound which presents preferably all of the following characteristics:

confers flexibility to the microcapsules;
shows resistance to physiological stresses;
is biocompatible;
has no or weak surface tension leading to a decrease in cellular adhesion;
can be covered by polymers thus leading to a modification of its permeability; and
can be of natural or synthetic origin.

Polymeric natural hydrogel compounds encompassed by the present invention can be agarose, alginate, chitosan or any other compound which preferably presents all of the above-mentioned characteristics. More particularly, the polymeric natural hydrogel compound of the present invention can comprise a chaining of two sugar moieties which form a binary copolymer non-ramificated and bound in a (1 to 4) fashion to the β-D-mannuronic acid monomer M) and to the α-L-guluronic acid (monomer G). The polymeric natural hydrogel compound of the present invention can present domains rich in homopolymers M, in homopolymers G, or in heterogenous domains MG. Preferably, the polymeric natural hydrogel compound of the present invention will present a high proportion in mannuronic acid.

Among polymeric synthetic hydrogel compounds which are contemplated by the present invention, one can note polyethylene glycol (PEG), poly(hydroxyethylmetacrylate-methyl-metacrylate (HEMA-MMA), acrylamide and the copolymer acrylonitrile (AN69). This type of polymeric compound presents the advantage of being non-soluble in aqueous solutions. This advantage becomes particularly important in the context of in vivo transplantation of microcapsules which then present a higher stability.

According to another aspect, the present invention relates to a pharmaceutical composition which comprises a plurality of the above-described microcapsules, each one of said microcapsules enclosing a material. This composition also comprises a pharmaceutically acceptable carrier.

The term "composition" as used herein is intended to encompass a product comprising the microcapsules of the present invention in the desired amounts.

By "pharmaceutically acceptable carrier", it will be understood that the carrier, diluter or excipient must be compatible with the microcapsule of the formulation and can be administered to a host without adverse effects. Suitable pharmaceutically acceptable carriers known in the art include, but are not limited to, sterile water, saline, glucose, dextrose, or buffered solutions. Carriers may include auxiliary agents including, but not limited to, diluters, stabilizers (i.e. sugars and amino acids), preservatives, wetting agents, emulsifying agents, pH buffering agents, viscosity enhancing additives, lactose, colors and the like. A preferable pharmaceutically acceptable carrier contemplated by the present invention is a culture medium, preferably a serum-free culture medium, such as the UltraCULTURE medium (Biowhittaker, Md.), preferably supplemented with 1% penicilline-streptomycin-glutamine.

B) Method of Microencapsulation

According to another aspect, the present invention relates to a method for microencapsulating a beaded material. This method comprises the steps of:
  a) providing a material enclosed within a bead to obtain a beaded material;
  b) covering the beaded material with a semi-permeable layer made of a polycation cross-linking derivative, to obtain a product; and
  c) covalently linking the beaded material to the semi-permeable layer.

Although step b) of covering the beaded material with a semi-permeable layer can be obtained by different ways well known in the art, the present invention preferably contemplates to incubate the beaded material with a polycation cross-linking derivative, to form said semi-permeable layer. This step of incubation preferably results in the beaded material being covered over substantially its entire surface with the semi-permeable layer made of the polycation cross-linking derivative.

Furthermore, step c) of this method of microencapsulation is preferably accomplished by a reaction between the beaded material and the semi-permeable layer. More specifically, this reaction produces covalent bonds between the negatively-charged compound of the beaded material and the polycation cross-linking derivative of the semi-permeable layer.

According to a preferred embodiment, the method of microencapsulation comprises, after step b), a step of covering, preferably by incubation, the product of step b) with a biocompatible layer. It will be understood that any other process known to one skilled in the art may be used for covering the product of step b) with the biocompatible layer. Moreover, step c) preferably further comprises a step of covalently linking the semi-permeable layer of the product of step b) to the biocompatible layer.

Although the step of "covalently linking" contemplated by the present invention can be achieved by any process known to one skilled in the art, the present invention preferably contemplates to expose the polycation cross-linking derivative of the semi-permeable layer to a predetermined dose of light, preferably UVA light and more preferably to a dose of light of at least about 2 kJ/m$^2$ and less than about 23 kJ/m$^2$. By "about", it is meant that the dose of light may slightly vary depending on the margin of error of the apparatus used to produce such light.

C) Method of Use

According to other aspects, the present invention relates to the use of an effective amount of a pharmaceutical composition of the invention for treating diabetes in a subject. By "treating diabetes", it is meant that both therapeutic and prophylactic or preventive measures are contemplated by the present invention to treat diabetes. More specifically, the present invention encompasses uses for a subject in need of treatment which includes a subject already presenting diabetes as well as a subject prone to present diabetes, or a subject in which diabetes is to be prevented.

As used herein, the term "subject" refers to any animal classified as a mammal, including humans, domestic and farm animals, and zoo, sports, or pet animals, such as dogs, horses, cats, cows, pigs, etc, in whom treating diabetes is desired.

The term "effective amount" means the amount of composition that will elicit the biological or clinical response of a tissue, system, animal or human that is being sought by the researcher, veterinarian, medical doctor or other clinician. In other words, such an effective amount of a composition for treating diabetes is an amount that is sufficient to ameliorate, or in some manner reduce the symptoms and/or the biological and biochemical anomalies associated with the disease. Such amount may be administered as a single dosage or may be administered according to a regimen, whereby it is effective. The amount may cure the disease but, typically, is administered in order to alleviate the symptoms and to normalize the biological and biochemical parameters associated with the disease, particularly the blood glucose level, while avoiding hypoglycaemia. This is possible because insulin secretion by microencapsulated insulin-secreting cells is modulated, in a minute-to-minute manner, according to the blood glucose level in the surrounding environment. This effect may be either transient or permanent. It will be understood that the term "permanent", as used herein, means until the animal, including humans, dies from a cause other than hyperglycaemia, and at a moment when the blood glucose level is still normal. It will also be understood that the duration of treatment effectiveness will most probably depend upon the survival of microencapsulated cells, since the microcapsules of the present invention are very unlikely to be damaged or destroyed during a lifetime, in the environment of a living body.

The expression "administering a" composition should be understood to mean providing a microencapsulated material of the invention or a composition of the invention to the subject in need of treatment.

The composition of the invention may be given to a subject through various routes of administration. For instance, the composition may be administered parenterally, for example by injections into the peritoneum, the subcutaneous space, or different organs, such as the liver, the spleen, the intestinal mucosa, the omentum, various muscles or into bio-artificial sites, developed especially for such implantations. These implantations could be performed through the transcutaneous, intravenous, intra-arterial routes or directly into the organ interstitial tissue. They could be done by transcutaneous injections, for certain sites preferably under radioscopic visualization, by laparoscopy, or by conventional surgery. Suitable dosages will vary, depending upon factors such as the amount of each of the components in the composition, the desired effect (fast or long term), the disease or disorder to be treated, the route of administration and the age and weight of the subject to be treated. Anyhow, for administering the composition of the invention, methods well known in the art may be used.

EXAMPLES

The following example is illustrative of the wide range of applicability of the present invention and is not intended to limit its scope. Modifications and variations can be made therein without departing from the spirit and scope of the invention. Although any method and material similar or equivalent to those described herein can be used in the practice for testing of the present invention, the preferred methods and materials are described.

Example 1

Preparation of a Polycation Cross-Linking Derivative According to a Preferred Embodiment of the Present Invention Preparation of polycation cross-linking derivatives according to a preferred embodiment of the present invention was performed in a dark room until UVA illumination. The photoactivatable cross-linking agent (cross-linker) Sulfo-SANPAH or ANB-NOS, as shown in FIGS. 1A and 1B, was dissolved in dimethylsulfoxide (DMSO), mixed with the polycation poly-L-lysine (PLL) dissolved in 0,2M borate buffer pH 8,4, at a ratio between the cross-linker and PLL of 1:20, remaining 3 hours at room temperature and kept overnight at 4° C. The polycation cross-linking derivative thus produced, namely PLL-Sulfo-SANPAH or PLL-ANB-NOS, was purified from residual reaction products by dialysis against NaCl 0,9% (w/v), using a 6000–8000 Da molecular weight cut-off membrane (Spectrum Laboratories, CA), at 4° C. for two days with four medium changes. The polycation cross-linking derivative was quantified with MicroBCA Protein Assay (Pierce, Rochford, Ill.) and diluted with saline at the appropriate concentration.

Example 2

Figure 2:
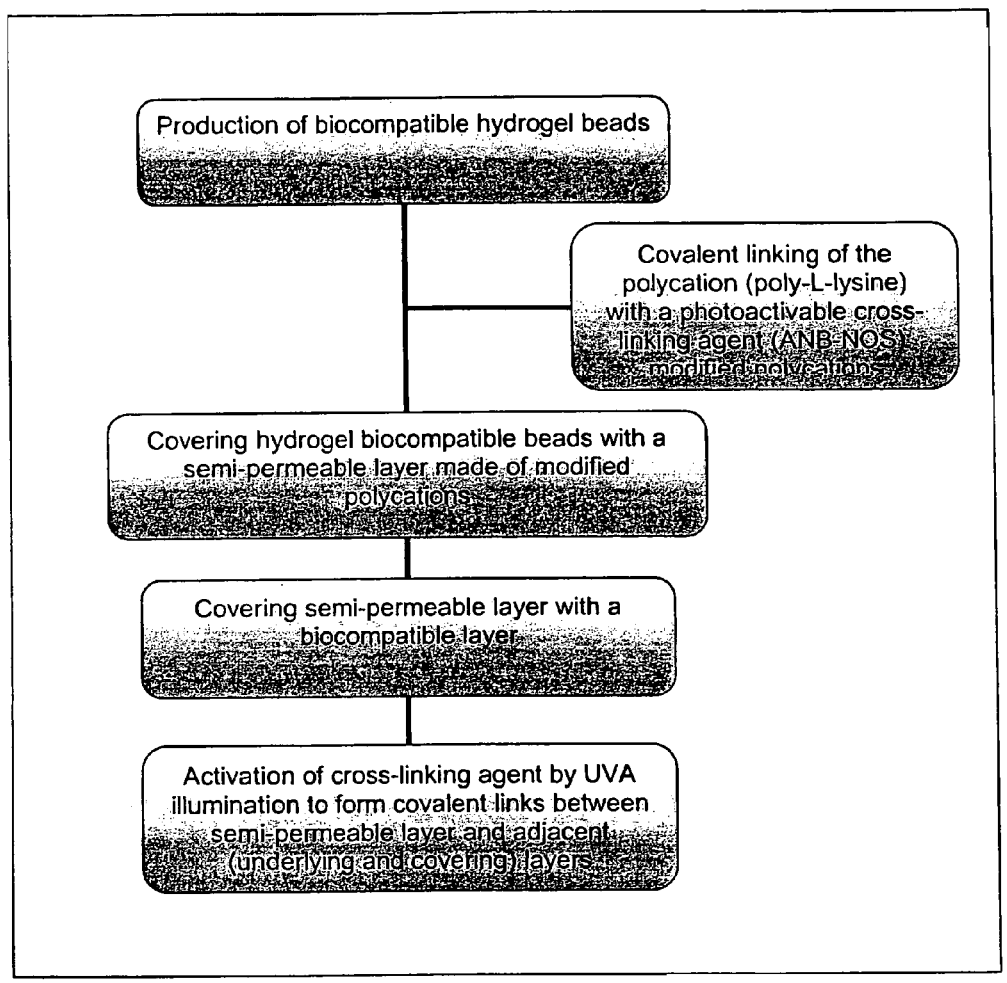
FIG. 2 is a schematic representation of the steps required in the formation of semi-permeable microcapsules with covalently cross-linked layers, according to a preferred embodiment of the present invention.
Figure 3:
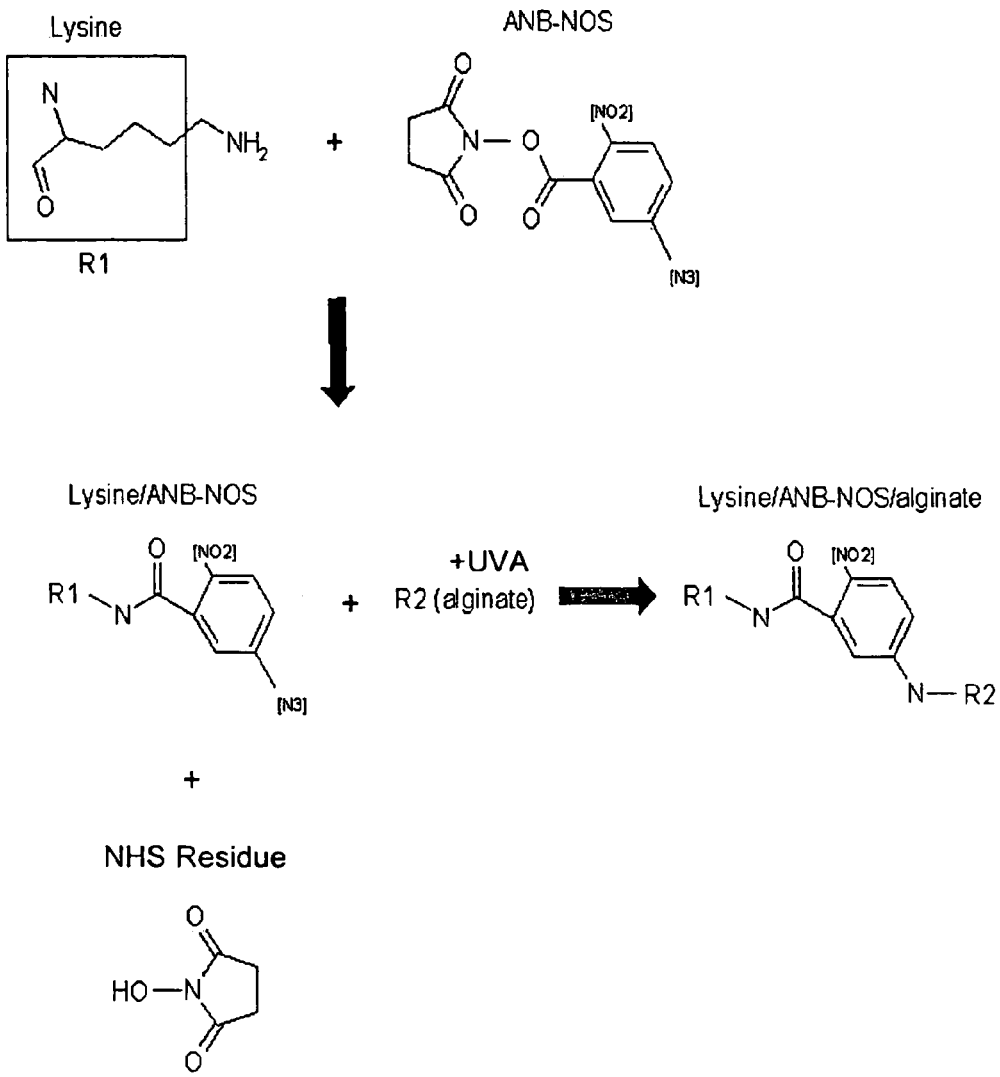
FIG. 3 is a schematic representation of the chemical reactions involved in formation of microcapsules cross-linked with ANB-NOS, according to a preferred embodiment of the present invention.

Preparation of a Microcapsule According to a Preferred Embodiment of the Present Invention The microcapsules were preferably prepared as described (Fritschy, W. M. et al. *Effect of alginate-polylysine-alginate microencapsulation on in vitro insulin release from rat pancreatic islets*. Diabetes 40(1): p. 37–43. 1991), with the following modifications. A schematic representation of the steps of such preparation is shown in FIG. 2. More specifically, a sterile solution of 1.8% purified sodium alginate was extruded into a bath of 100 mM calcium lactate buffered with HEPES. The calcium alginate gelled beads were incubated into a 0.05% w/v PLL or PLL-crosslinker derivative solution for 5 minutes, washed with saline and incubated 5 minutes into 0,18% w/v sodium alginate. Finally, microcapsules were washed twice with saline. Steps involving PLL cross-linking derivative were performed under dim light. Microcapsules were then submitted to UVA light exposure (Blacklight 25W #F25T8-BL, UV product, Upland, Calif.) at 2 kJ/m$^2$. Microcapsules prepared without a photoactivatable cross-linking agent and UVA illumination were used as controls. A schematic view of the chemical reactions involved in the above-mentioned preparation is shown in FIG. 3.

Referring again to FIG. 3, it can be seen that the N-hydroxysuccinimide residue of ANB-NOS was first covalently linked to the primary amine of PLL, before the presence of living cells to be eventually embedded within the microcapsules of the invention. This exothermic chemical reaction would damage living cells. When islets of Langherans were to be embedded within the initial bead, they were initially immobilised in a calcium alginate core, incubated in PLL cross-linking derivative and in (diluted) alginate again to form the biocompatible layer. Then, microcapsules were illuminated with a UVA lamp. Upon UVA exposure, the photoactivatable phenyl azide residue of the cross-linker reacted rapidly within a carbon-carbon or a carbon-hydrogen bond into the alginate chemical structure, creating a covalent link between PLL and alginate from both the microcapsule core and outer biocompatible layer. The latter reaction is not harmful for living cells, provided a high UVA dose, such as one equal to or higher than 23 kJ/m$^2$, is not used.

The morphological parameters of preferred microcapsules according to the present invention are presented hereinbelow in Table 1. It can be appreciated that all three types of microcapsules, namely standards, cross-linked with S-SANPAH and cross-linked with ANB-NOS, present a round shape and have a diameter of about 318 μm. However, microcapsules cross-linked with S-SANPAH showed a higher membrane thickness and a higher swelling percentage, in comparison with the two other types of microcapsules.

TABLE 1

Morph logical parameters of micr capsules according to preferred embodiments of the present invention.

| Parameters | Standard | Microcapsules with S-SANPAH | with ANB-NOS |
|---|---|---|---|
| Diameter (μm) | 323.2 ± 7.1 | 308.3 ± 5.8 | 318.4 ± 8.8 |
| Membrane Thickness (μm) | 4.3 ± 1.0 | ND | 4.6 ± 1.4 |
| Swelling (%) | 28.3 | 36.0 | 26.4 |
| Shape | Round | Round | Round |

ND: not determined.

Example 3

Detection of Covalent Links Between the Polycation and the Negatively-Charged Compound, According to a Preferred Embodiment of the Present Invention The presence of covalent bonds was confirmed by incubation in a strong alkaline solution. Microcapsules were incubated in this solution for at least 5 minutes. The rationale behind such a procedure was that the electrostatic interactions between the positively-charged PLL and the negatively-charged alginate can be interrupted by neutralizing one of the charged groups. Accordingly, since PLL residues have an iso-electric point of 10.54, a suspension of microcapsules in saline was adjusted to pH 12 by adding 1/20 volume of 2 M glycine buffer pH 12 (2 M glycine, 14 mM NaCl, 2N NaOH). Morphological changes were followed by microscopic examination.

Figure 4A:
FIGS. 4A to 4E are microscopic views of standard microcapsules and microcapsules according to a preferred embodiment of the invention upon incubation in a strong alkaline pH (pH=12) solution. A. Standard microcapsules, 63×, before incubation. B. Standard microcapsules in glycine buffer pH 12, 63×, a few seconds after addition of the alkaline buffer C. Standard microcapsules in glycine buffer pH12 after 45 seconds. D. microcapsules of the invention before incubation, 100×. E. microcapsules of the invention in glycine buffer pH 12 after two years, 100×.
Figure 4B:
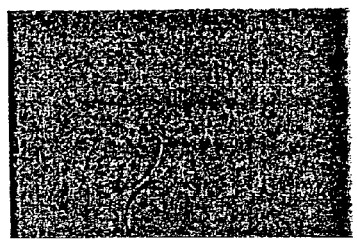
Figure 4C:
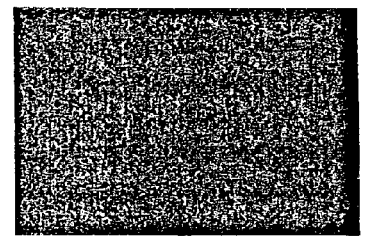
Figure 4D:
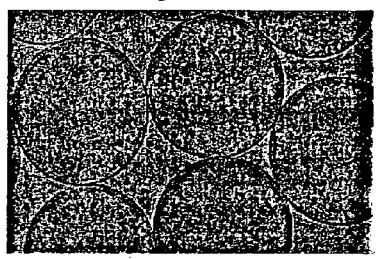
Figure 4E:
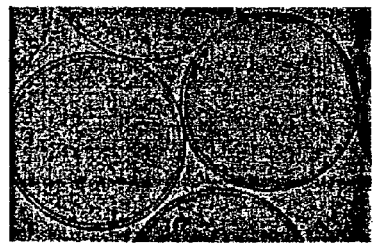

Referring to FIG. 4, one can appreciate that standard microcapsules, used as controls (FIG. 4A), rapidly dissolved and disappeared in the solution within 45 seconds (FIGS. 4B and 4C). In contrast, microcapsules prepared with PLL-ANB-NOS resisted to an incubation in this alkaline solution, with a swelling percentage of approximately 39% (FIGS. 4D and 4E), and a microcapsule recovery rate of 96.5±4.3%. After 2 years in the alkaline buffer, they remained intact, retaining a normal round shape and a smooth surface.

Of note, using the above-mentioned alkaline dissolution test, two similar photoactivatable cross-linkers were evaluated: ANB-NOS and sulfosuccinimidyl 6-(4'-azido-2'-nitrophenylamino) hexanoate (Sulfo-SANPAH), as mentioned in Example 1. The only difference between these two molecules is the length of the chain joining the two reactive groups. Sulfo-SANPAH possesses 6 carbon atoms and one nitrogen atom, forming a spacer arm of 18.2 Å. Since ANB-NOS has no spacer arm, the distance between the two reactive residues is only 7.7 Å. When microcapsules made with sulfo-SANPAH-derived PLL were submitted to the alkaline dissolution test, they completely disappeared from the solution within a few minutes (data not shown).

Example 4

Evaluation of Microcapsule Physical and Functional Characteristics

Microcapsule mechanical resistance was evaluated, according to a preferred embodiment of the present invention, using a quantitative method previously reported in Leblond, F. A., Tessier, J. & Halle, J. P. *Quantitative method for the evaluation of biomicrocapsule resistance to mechanical stress*. Biomaterials 17(21): p. 2097–2102, 1996, although with the following modifications.

Microcapsules were submitted to a mechanical stress test. Briefly, microcapsules were prepared with sodium alginate containing 0,2% w/v 2,000 kDa FITC-labelled dextran. These large size dextrans have been shown to be withheld inside intact microcapsules indefinitely. Measurement of fluorescence in the supernatant is linearly and very accurately correlated with the number of broken microcapsules. The accuracy of this measurement is such that one single broken microcapsule dissolved in 10 ml of solution can be detected. A suspension of 1000 of these microcapsules in saline was mixed with 225 borosilicate glass beads of 3 mm in diameter, in 15 ml polystyrene tubes. They were submitted to continuous shaking on a rotatory vertical agitator at 35 rpm for 72 hours. At this speed, the centrifugal force is relatively weak and, while the tube turns upside down, the glass beads and microcapsules move rapidly from one end of the tube to the other, submitting microcapsules to thousands of strokes and crushes between beads and the tube wall.

During this test, microcapsules containing 2,000 kDa FITC-labelled dextran were submitted to more and stronger mechanical stresses than they are likely to encounter during a lifetime in an implantation site such as the peritoneum and in bioreactors.

Additionally, in order to test the effect of UVA dose illumination during the microcapsule cross-linking step, two doses of UVA light were evaluated.

Figure 5:
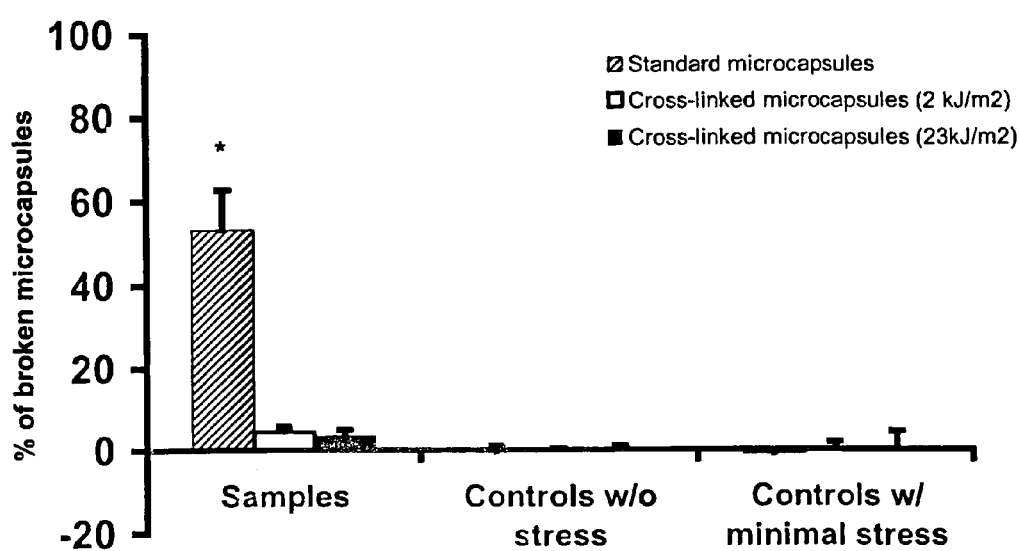
FIG. 5 is a graph showing the mechanical resistance of microcapsules according to a preferred embodiment of the invention.

As shown in FIG. 5, the percentage of broken microcapsules was calculated by quantifying the amount of FITC-labelled dextran in the supernatant and in intact microcapsules. For this purpose, standard microcapsules were dissolved in 20 ml of 0.9% NaCl buffered to pH12 with 0.1 M glycine, as described. The following modifications to the original techniques were made. Since this method could not break cross-linked microcapsules, the latter were digested by the addition of HCl 1.2 N and incubated at 100° C. for 18 minutes. Such conditions are known not to break the covalent links, but to break links between atoms within the alginate or PLL molecules. For normalization, the samples of the standard curve were digested in same conditions.

The percentage of broken microcapsules was about 22-fold lower for microcapsules cross-linked using ANB-NOS under 2 and 23 kJ/m$^2$ (4.4% and 3.4%, respectively) than for standard microcapsules (53.3%), whereas all controls showed negligible amounts of dextran in the supernatant (less than 0.2%), confirming that there was no dextran leaking out from unbroken microcapsules (FIG. 5). Moreover, FIG. 5 shows that none of the microcapsule preparations was abnormally fragile.

Example 5

Evaluation of Microcapsule Permeability Using Molecular Weight Cut-Off (MWCO)

According to a preferred embodiment of the invention, microcapsule permeability was evaluated using size exclusion chromatography as previously described (Brissova, M. et al. *Evaluation of microcapsule permeability via inverse size exclusion chromatography*. Anal Biochem 242: p. 104–111, 1996; Robitaille R. et al. *Studies on small (<350 µm) alginate-poly-L-lysine microcapsules. V. Determination of carbohydrate and protein permeation through microcapsules by reverse size exclusion chromatography*. J Biomed Mater Res, 50: p.420–427, 2000; and Steward, W. W. & Swaisgood, E. *Characterization of calcium alginate pore diameter by size-exclusion chromatography using protein standards*. Enzyme Microbiology & Technology 15: p. 922–927, 1993). A column was mounted using the microcapsules under study. FITC-dextran (2,000 kDa) was used to measure the column's dead or void volume (Vo) and glucose (180 kDa) was used to determine the column's total volume (Vt). Markers of different molecular weight (MW) and viscosity radius (Rη) were sequentially run on the column: dextrans (MW: 2,000 kDa, 19 kDa, 4.4 kDa; Rη 34.2 nm, 3.4 nm, 1.7 nm, respectively); proteins: bovine serum albumin (MW 66 kDa; Rη 3.4 nm), ovalbumin (MW: 45 kDa; Rη 2.9 nm) and carboxypeptidase (MW 35.2 kDa; Rη 2.7 nm). For each marker, a partition chromatographic coefficient ($K_{sec}$) was calculated using the following formula: $K_{sec}=(Ve-Vo)/(Vt-Vo)$, where Ve is the marker retention volume (corresponding to the peak of the elution profile of the marker). Freely permeable markers have a $K_{sec}$ value near 1.0. Excluded markers have a $K_{sec}$ value near 0.

TABLE 2

Permeability of standard and cross-linked microcapsules, according to a preferred embodiment of the present invention.

| Molecules | MW (kDa) | Rη | Standard $K_{sec}$ | Profile | Cross-linked $K_{sec}$ | Profile |
|---|---|---|---|---|---|---|
| Dextran 2000* | 2000 | 34.2 | 0.0 | excluded | 0.0 | excluded |
| Dextran 19 | 19 | 3.4 | 0.0 | excluded | 0.1 | excluded |
| Bovine Albumin | 66 | 3.4 | 0.0 | excluded | 0.1 | excluded |
| Ovalbumin | 45 | 2.9 | 0.0 | excluded | 0.1 | excluded |
| Carboxypeptidase | 35.25 | 2.7 | 0.9 | included | 1.0 | included |
| Dextran 4.4** | 4.4 | 1.7 | 1.0 | included | 1.0 | included |

*molecule excluded from the microcapsules, considered as the dead volume of the column;
**molecules which can penetrate into the microcapsules, considered as the total volume of the column.

As shown hereinabove in Table 2, covalent cross-linking of APA membranes had no significant effect on membrane permeability. More specifically, both covalently cross-linked and standard microcapsules excluded [partition chromatographic coefficient ($K_{sec}$)≈0.1] dextrans with a MW≧19 kDa [viscosity radius (Rη)≧3.4 nm] and proteins with a MW≧45 kDa (Rη≧2.9 nm), whereas dextrans with a MW≦4.4 kDa (Rη≦1.7 nm) and proteins with a MW≦35.2 kDa (Rη≦2.7 nm), diffused freely ($K_{sec}$≈1.0) through both types of membranes. The apparent discrepancy between the permeation of carbohydrates and proteins is due to the fact that dextrans are linear neutral molecules whereas proteins are globular charged molecules. It is noteworthy that the Rη provided a better relative estimation of molecule diameters than the MW.

Example 6

Effect of Microencapsulation on the Survival of Microencapsulated Islets of Langerhans Microencapsulation was performed preferably with islets of Langherans. Islets from Wistar rats (300–400 g) were isolated using a published method (Lacy, P. E. & Kostianovsky, M. *Method for the isolation of intact islets of Langerhans from the rat pancreas*. Diabetes 16: p. 35–39, 1967) and encapsulated in standard or covalently linked APA microcapsules.

Briefly, rat pancreatic tissues were infused via the common bile duct with Hank's balanced salt solution at 4° C., minced on ice and digested with a collagenase type V solution (7,5 mg/ml) and Dnase I (0,25 g/ml) for 5 minutes at 37° C., with shaking. The islets thus freed from the pancreatic tissue were then purified on a discontinuous Ficoll gradient obtained by dissolving 500 g Ficoll DL-400 (Pharmacia, Upsala, Sweden) in 1,5 L of the euro-collin perfusion solution (Frenesius AG, Bad Homburg, Germany) at final densities of 1,108; 1,096; 1,069 and 1,037. The islets were then handpicked under an inverted light microscope. Islet purity was between 95 and 98%. The islets were then cultured in an RPMI 1640 medium, 11 mM glucose (Invitrogen Life Technologies, Burlington, ON, Canada) supplemented with 10% foetal calf serum (Invitrogen Life Technologies, Burlington, ON, Canada) and 100 units of penicillin-streptomycin-glutamine (Invitrogen Life Technologies, Burlington, ON, Canada) overnight at 27° C., 5% $CO_2$.

Cellular Encapsulation

The first step was to wash islets of Langerhans with a saline solution. The washed cells were then resuspended in an alginate solution 1,8% at a concentration of about 3000 islets/ml of alginate. Cells were entrapped in small alginate beads by extrusion of the alginate solution through a 25-gauge needle using an electrostatic droplet generator. The alginate beads fell into a 100-mM calcium lactate solution, which cross-linked the alginate to form gelled beads. The microcapsule membrane was formed by successively soaking the alginate beads in 0,05% poly-L-lysine (Sigma-Aldrich), standard or modified with a photoactivatable cross-linking agent, for 5 minutes and 0,18% alginate for 5 minutes. The microcapsules thus produced presented a diameter of 300 to 350 µm. Photoreticulation of microcapsules comprising a photoactivatable cross-linking agent was performed at two different UVA doses for the islets (2 and 23 $kJ/m^2$) on ice to minimize heat damage from UVA rays. Controls included non encapsulated islets exposed to the same UVA irradiation. All groups were cultured in CMRL 1066 medium (Invitrogen Life Technologies, Burlington, ON, Canada) supplemented with 10% foetal calf serum and 1% penicillin-streptomycin-glutamine (Invitrogen Life Technologies, Burlington, ON, Canada) overnight at 27° C., 5% $CO_2$, with medium changes performed every second day.

Figure 6:
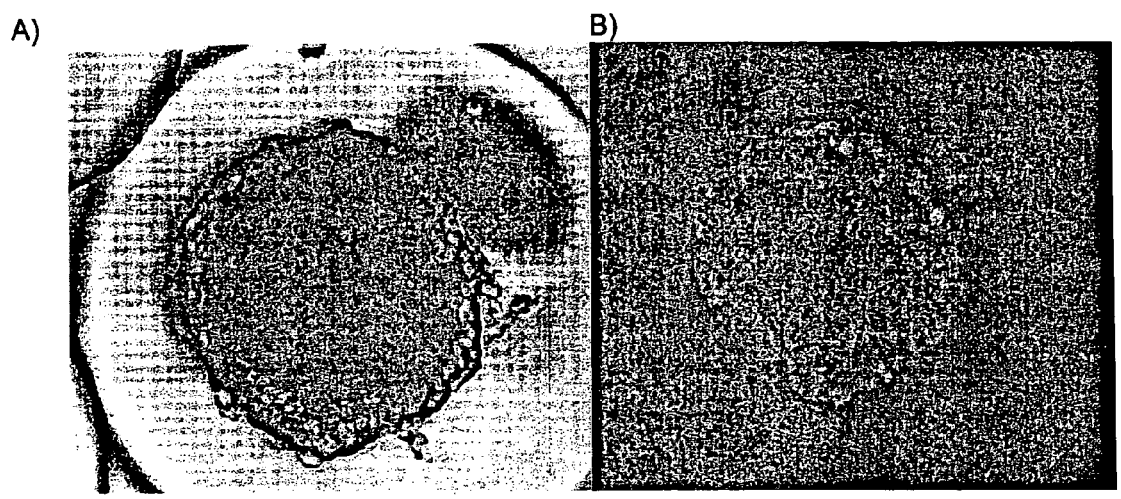
FIGS. 6A and 6B are microscopic views (100×) of an islet of Langerhans with a necrotic center (A) and of the same islet after incubation with acridine orange/propidium iodide (B).

Fresh (unstained) islets were examined under a stereomicroscope (Labovert FS, Leitz, Leica Canada, St-Laurent, QC, Canada) (FIG. 6A), and the number (%) and size of islets with necrotic centers were recorded as well as the diameter of the necrotic area. Concomitantly, the survival of microencapsulated islet cells was evaluated in vitro using dual staining with orange acridine and propidium iodide and observed under a fluorescent microscope (FIG. 6B). FIG. 6 thus shows a parallel between necrosis and viability of islets of Langerhans, as examined in unmanipulated state and after fluorescent staining.

Viability

Fluorescence microscopy was used, as previously described by Bank et al. (Bank, H. L. *Assessment of islet cell viability using fluorescent dyes*. Diabetologia 30: p. 812–816, 1987; and Bank, H. L. *Rapid assessment of islet viability with acridine orange and propidium iodide*. In Vitro Cell Dev Biol 24,: p. 266–273, 1988), to evaluate islet cell viability at the end of the incubation period. Briefly, aliquots of 100 microencapsulated islets were stained with acridine orange (0,01 mg/ml; Sigma-Aldrich) and propidium iodide (0,5 µg/ml; Sigma-Aldrich), for 15 minutes at room temperature while being protected from light. Islets were than evaluated under a fluorescence microscope and islets showing more than 50% of viable cells were considered viable. Viability was evaluated for standard and cross-linked microencapsulated islets as well as standard microencapsulated islets submitted to the same doses of UVA radiations used for cross-linked microencapsulated islets.

Figure 7:
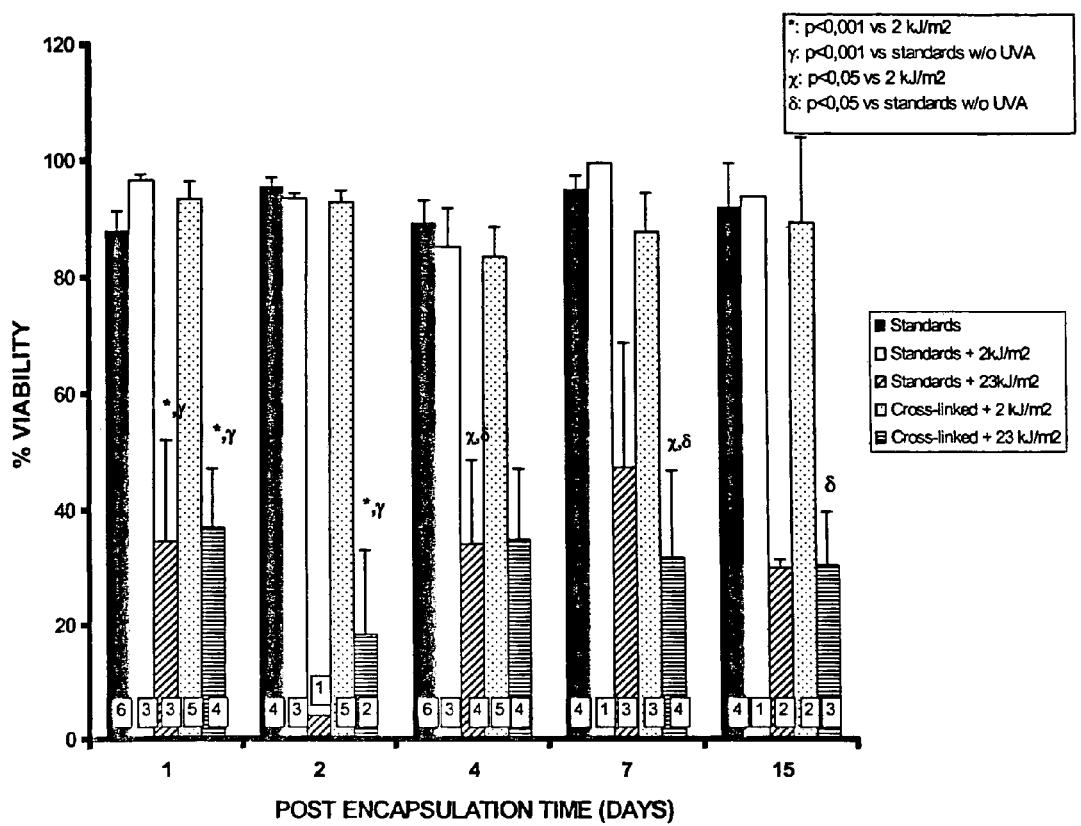
FIG. 7 is a graph showing the viability of islets of Langerhans embedded in a microcapsule according to a preferred embodiment of the invention.

The key step in one of the preferred microencapsulation processes is the generation of covalent links by UVA illumination. A wavelength of 320–350 nm, known to induce minimal cell damage, was selected. Potential cell damages were evaluated using a double stain viability test and the observation of necrotic centers on fresh islets under a stereomicroscope. As shown in FIG. 7, islet cell viability was evaluated at different time points, namely at 1, 2, 4, 7 and 15 days post-microencapsulation.

In initial studies, a 23 $kJ/m^2$ UVA dose, with or without ANB-NOS, decreased islet cell viability (FIG. 7), whereas ANB-NOS alone had no direct cytotoxicity. The cell damage was partially explained by the UV radiation thermal effect, since the preparation warmed up despite the fact it was on ice.

To investigate the hypothesis that the harmful effect is dose related, covalently linked microcapsules were produced, using a large range of UVA doses. A dose of 2 $kJ/m^2$, 11.5 fold smaller than the initial dose (23 $kJ/m^2$), was equally effective in generating covalent links and improving microcapsule resistance. This small dose was used (and compared with the high dose where indicated) for all the experiments reported in the present example, except for the MWCO studies of Example 5. The latter were not repeated, since even the high dose had no effect on this parameter. The smaller dose was as effective as the large dose in improving chemical and mechanical resistance. The effect did not seem to be progressive (FIG. 7); therefore, it suggests that the smaller dose induced the same level of covalent links as the larger dose.

Necrotic Centers

Figure 8:
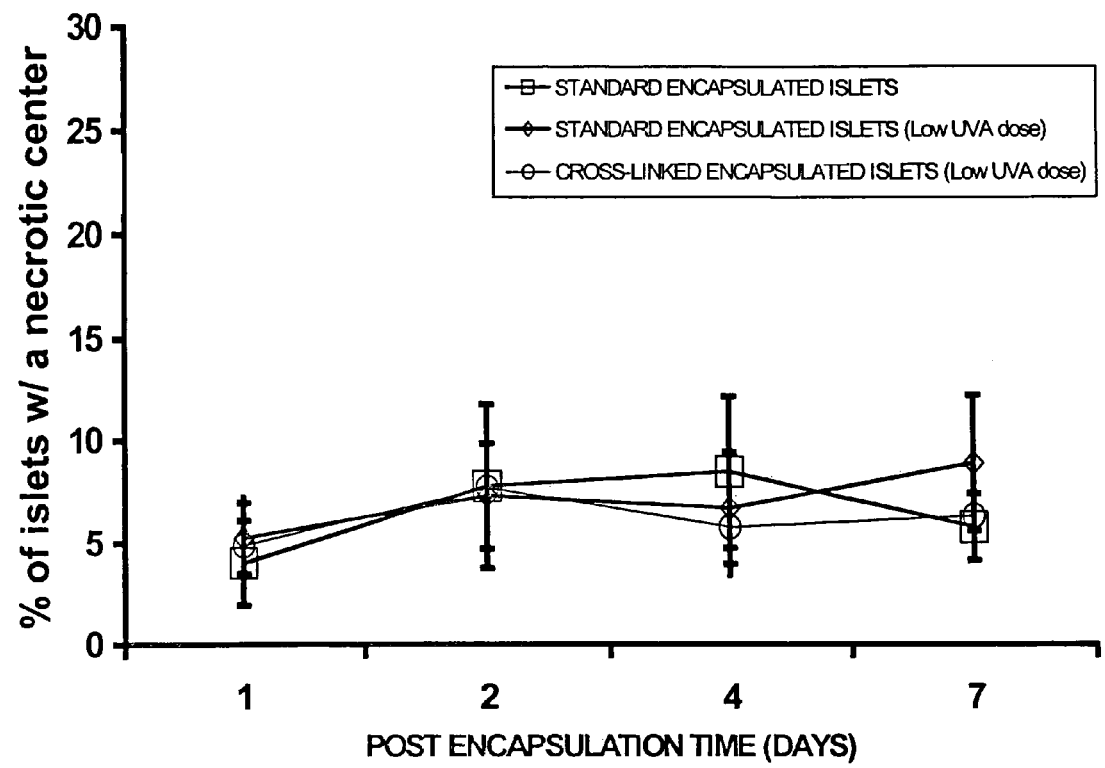
FIG. 8 is a graph showing the percentage of necrotic centers in islets of Langerhans embedded in a microcapsule according to a preferred embodiment of the invention.

As previously described (Ilieva, A. et al. *Pancreatic islet cell survival following islet isolation: the role of cellular interactions in the pancreas*. J Endocrinol 161: p. 357–364, 1999), the mechanism of islet cell death was characterized by evaluating the percentage of cells with a necrotic center as well as measuring the size of these cells and the diameter of the necrotic area. The necrotic center is characterized by the formation of a bold structure with sharply defined borders in the middle of the pancreatic islet. The increasing number of islets with a necrotic center was correlated with a decrease in islet viability. Necrotic centers were evaluated for both standard and cross-linked microencapsulated islets, according to the following kinetics i.e. 1, 2, 4 and 7 days of culture post-microencapsulation. Results of this evaluation are presented in FIG. 8.

CONCLUSION

The results of the viability tests (FIG. 7) and the evaluation of necrotic centers (FIG. 8) showed that the illumination of encapsulated islets with a 2 kJ/m$^2$ dose of UVA, with or without ANB-NOS, did not affect islet cell viability as compared with standard microcapsules (~90% viability and 15% necrotic centers for each of the 3 conditions under study).

Example 7

Evaluation of In Vivo Islet Function Upon Microencapsulation

Diabetes Induction in Mice

Diabetes was induced in C57Bl/6 mice (Charles River, St-Constant, QC, Canada) by injecting them intraperitoneally with 185 mg/ml per kg of streptozotocin (STZ) solution (Sigma-Aldrich). This STZ solution specifically destroys β pancreatic cells and simulates type 1-diabetes in its recipients. Diabetic mice (blood glucose>20 mM for 2 consecutive days) were transplanted with microencapsulated islets (standard or cross-linked), one week after the onset of diabetes. Control groups included diabetic mice transplanted with non-microencapsulated islets, and non-transplanted mice.

Microencapsulated Islet Transplantation

Microencapsulated and non-encapsulated islets were washed and resuspended in a physiological saline solution. Grafts containing 500 islet equivalents (it will be understood by any person skilled in the art that "500 islet equivalents" are equivalent to the volume of 500 islets of 150-μm diameter) were then injected intraperitoneally in mice with a 16-gauge catheter. After transplantation, blood glucose level of mice was followed daily the first week post-transplantation and twice weekly the following weeks, with a glucose analyzer (ELITE, Bayer, Toronto, ON, Canada). Mice showing two consecutive blood glucose levels under 11 mM were considered normoglycemic. Thereafter, normoglycemic mice with two consecutive blood glucose levels above 11 mM were considered to present a recurrence in their diabetes.

Figure 9:
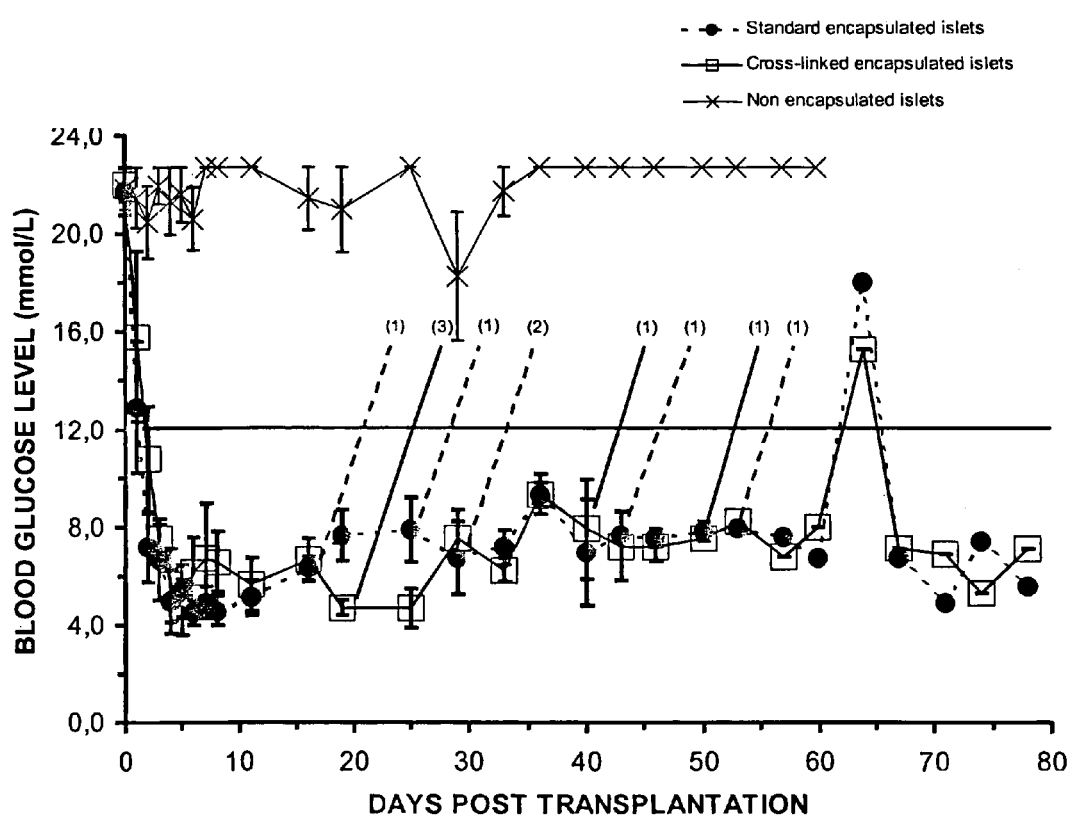
FIG. 9 is a graph showing the blood glucose level results of diabetic mice following xenotransplantation of islets of Langerhans embedded in microcapsules according to a preferred embodiment of the invention.

Referring to FIG. 9, one can appreciate the follow-up in time of glycaemia in mice upon transplantation. More precisely, FIG. 9 shows that mice transplanted with microencapsulated islets (standard or cross-linked) shifted from a diabetic state, with glucose in the range of 22 mmol/L, to a euglycemic state with normal glucose levels in the range of 6 mmol/L, less than three days following transplantation. In addition, one can also appreciate that diabetic mice transplanted with non-encapsulated islets did not present remission of their disease, with glucose levels remaining at 19 to 23 mmol/L all through the experiments.

In the case of transplantations made with the two different types of microcapsules, relapses were observed starting from 16 days post-transplantation for standard microcapsules, and from 19 days for cross-linked microcapsules. Data for relapsing mice are presented by the oblique bars and their number is in parentheses. There are no significant differences between the two groups, with regards to the relapse rate.

Figure 10:
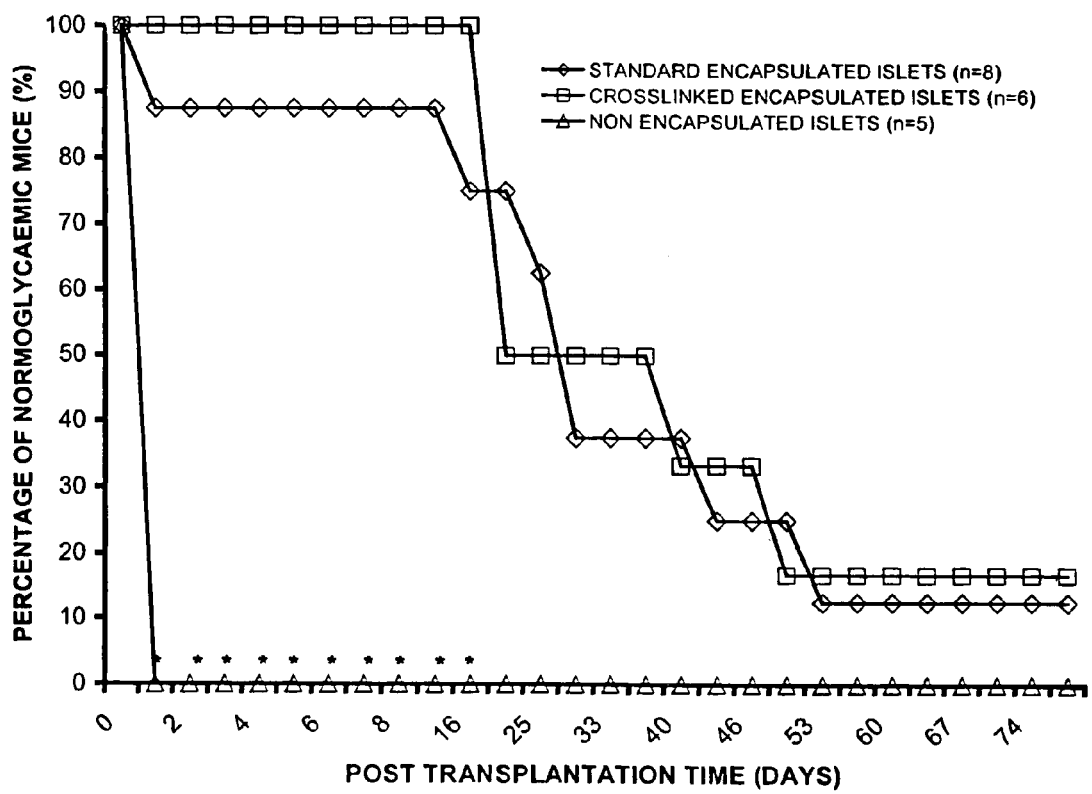
FIG. 10 is a graph showing the percentage of diabetic mice maintaining euglycaemia, following xenotransplantation of islets of Langerhans embedded in microcapsules according to a preferred embodiment of the invention.

Referring now to FIG. 10, it can be noted that the percentage of mice maintaining euglycaemia was evaluated in time, post-transplantation, for the 3 groups of mice under study. None of the mice transplanted with non encapsulated islets were euglycaemic from 24 hours after transplantation. There was no significant difference in the percentage of euglycaemic mice whether they were transplanted with either standard or covalently cross-linked microcapsules.

Example 8

Effect of Microencapsulation on Function of Microencapsulated Hepatocytes

Rat Hepatocyte Isolation

Hepatocytes were isolated from Sprague-Dawley rats (250–350 g, Charles River, St-Constant, QC, Canada) according to the method published by Seglen et al. (Seglen, P. O., *Preparation of isolated rat liver cells*. Methods Cell Biol 13: p. 29–83, 1976). Briefly, rat livers NaCl, 5mM KCl, 1% glucose, 0,4 mM $KH_2PO_4$, 0,2 mM $Na_2HCO_3$ at pH 7,4) with 0,1 U/ml heparin (Sigma, St-Louis, Mo.) and 0,5 mM EGTA via the portal vein. Thereafter, the hepatic tissue was digested by perfusing the liver with a Hank's solution comprising 5 mg/ml collagenase D (Roche, Laval, QC), 1,2 mM MgSO4, 1,8 mM CaCl2 and 7,5 μg/ml trypsin inhibitor (Sigma, St-Louis, Mo.). The tissue was collected and hepatic cells were extracted therefrom. Live cells were then separated from dead ones on a 40% Percoll gradient (Amersham Biosciences Inc., Baie d'Urfé, QC, Canada). The viability of hepatocytes was evaluated with a Trypan blue dye.

Cellular Encapsulation

The isolated rat hepatocytes were then resuspended in an alginate solution 1,8% at a concentration of about $2,5 \times 10^6$ hepatocytes/ml of alginate. From this point forward, the microencapsulation process was the same as the one described for the above-mentioned islets of Langerhans. The microencapsulated rat hepatocytes thus obtained were then evaluated for their function by the sodium 3'-[1-(phenyl-amino-carbonyl)-3,4-tetrazolium]-bis (4-methoxy-6-nitro)-benzene sulfonic acid hydrate or XTT assay (Roche Diagnostics, Laval, QC, Canada).

Hepatocyte Function by the XTT Assay

Figure 11:
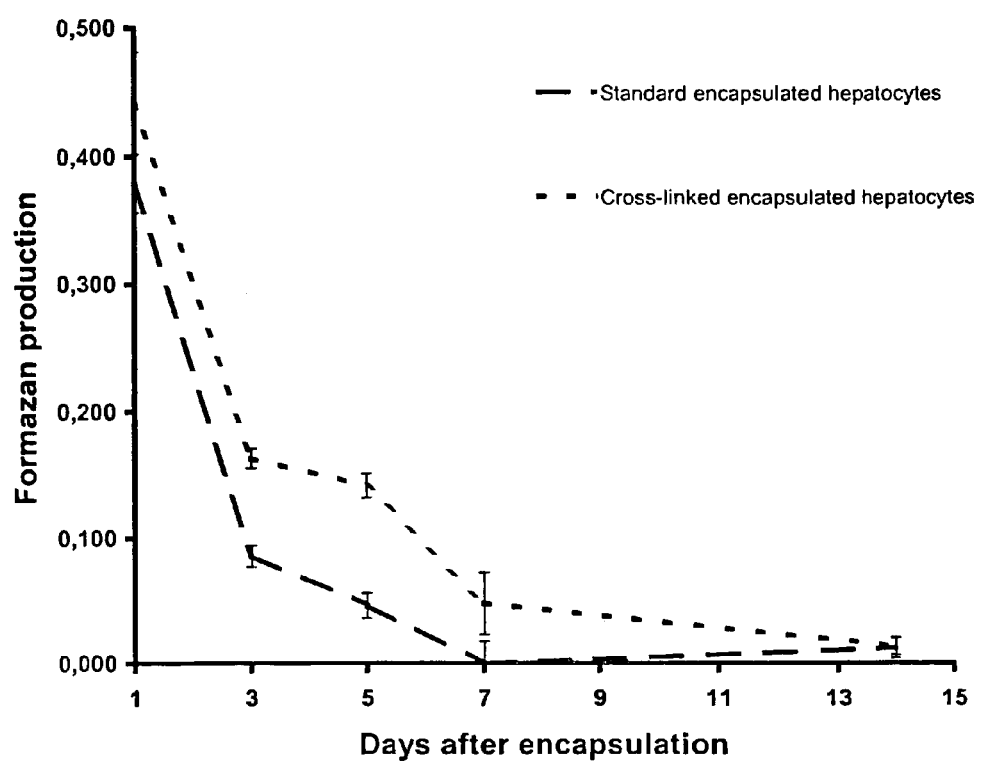
FIG. 11 is a graph showing the effect of microcapsulation on function of hepatocytes embedded in microcapsules according to a preferred embodiment of the invention.

Hepatocyte function was assessed by the sodium 3'-[1-(phenyl-amino-carbonyl)-3,4-tetrazolium]-bis (4-methoxy-6-nitro)-benzene sulfonic acid hydrate or XTT assay (Roche Diagnostics, Laval, QC, Canada). An aliquot of about 30,000 encapsulated cells was incubated in a William's culture medium comprising 0,3 mg/ml of XTT in a 96-well plate for 6 hours at 37° C. and 5% $CO_2$. XTT is metabolized by mitochondria of viable cells to form soluble formazan, which can be detected with an ELISA plate reader (absorbance wavelength: 450 nm; reference wavelength: 620 nm). The difference in the amount of formazan produced between standard and cross-linked microcapsules was followed at 1, 3, 5, 7 and 14 days of culture post-encapsulation, as shown in FIG. 11. The formazan production was normalized with values obtained with an absorbance wavelength without cells.

Referring to FIG. 11, it can be appreciated that covalent cross-linking does not impede on hepatocyte function.

Example 9

Statistical Analysis

All of the above-mentioned tests and assays were evaluated according to the following statistical analysis. More specifically, results are expressed as mean±SEM. The differences between experimental groups were analyzed by unpaired Student's t test with p values less than 0.05 considered significant.

Mouse survival following transplantation was analyzed by $X^2$ test with P<0,05 considered significant.

What is claimed is:

1. A method for microencapsulating a beaded material, said method comprising the steps of:
   a) providing a material enclosed within a bead to obtain a beaded material;
   b) covering the beaded material with a semi-permeable layer made of a polycation cross-linking derivative to obtain a product, wherein said polycation cross-linking derivative is obtained by covalently linking said polycation with a photoactivable cross-linking agent;
   c) covering the product of step b) with a biocompatible layer, and
   d) activating said cross-linking agent to covalently link said semi-permeable layer of the product of step b) to said beaded material and said biocompatible layer.

2. The method of claim 1 comprising, prior to step b), a step of covalently linking a polycation to a photoactivatable cross-linking agent to obtain the polycation cross-linking derivative of step b), said photoactivatable cross-linking agent comprising:
   a N-hydroxysuccinimide ester group; and
   a phenyl azide group.

3. The method of claim 1, wherein step d) comprises exposing the polycation cross-linking derivative of the semi-permeable layer to a predetermined dose of light.

4. The method of claim 3, wherein the light is UVA light.

5. The method of claim 4, wherein the predetermined dose of light is at least about 2 kJ/m$^2$ and less than about 23 kJ/m$^2$.

6. The method of claim 1, wherein the bead and the biocompatible layer comprise a negatively-charged compound.

7. The method of claim 6, wherein the negatively-charged compound is a hydrogel.

8. The method of claim 7, wherein the hydrogel is alginate.

9. The method of claim 2, wherein the polycation is poly-L-lysine.

10. The method of claim 2, wherein the photoactivatable cross-linking agent is N-5-Azido-2-nitrobenzoyloxysuccinimide (ANB-NOS).

11. The method of claim 2, wherein the polycation is poly-L-lysine and the photoactivatable cross-linking agent is N-5-Azido-2-nitrobenzoyloxy-succinimide (ANB-NOS).

12. The method of claim 1, wherein the poly-L-lysine and the ANB-NOS are mixed together in a 1:20 ratio.

13. The method of claim 1, wherein said beaded material is beaded living cells.

14. The method of claim 13, wherein said living cells are insulin-producing cells.

15. The method of claim 14, wherein said insulin-producing cells are comprised in islets of Langerhans.

16. A semi-permeable microcapsule comprising: a bead suited to enclose a material;
   a semi-permeable layer covering the bead, said semi-permeable layer being made of a polycation cross-linking derivative covalently linked to the bead; and a biocompatible layer covering said semi-permeable layer, said biocompatible layer being covalently linked to the polycation cross-linking derivative of said semi-permeable layer, wherein said polycation cross-linking derivative is obtained from covalent linking of said polycation with a photoactivable cross linking agent.

17. The microcapsule of claim 16, wherein said polycation cross-linking derivative is a polycation covalently linked to a photoactivatable cross-linking agent, said agent comprising:
   a N-hydroxysuccinimide ester group; and
   a phenyl azide group.

18. The microcapsule of claim 16, wherein the bead and the biocompatible layer comprise a negatively-charged compound.

19. The microcapsule of claim 18, wherein the compound is a hydrogel.

20. The microcapsule of claim 19, wherein the hydrogel is alginate.

21. The microcapsule of claim 17, wherein the polycation is poly-L-lysine.

22. The microcapsule of claim 17, wherein the photoactivatable cross-linking agent is N-5-Azido-2-nitrobenzoyloxysuccinimide (ANB-NOS).

23. The microcapsule of claim 17, wherein the polycation is poly-L-lysine and the photoactivatable cross-linking agent is N-5-Azido-2-nitrobenzoyloxy-succinimide (ANB-NOS).

24. The microcapsule of claim 23, wherein the poly-L-lysine and the ANB-NOS are in a 1:20 ratio.

25. The microcapsule of claim 16, wherein said microcapsule allows passage of molecules with a defined viscosity radius.

26. The microcapsule of claim 25, wherein said viscosity radius is equal or inferior to about 2.7 nm.

27. The microcapsule of claim 16, wherein said material is living cells.

28. The microcapsule of claim 27, wherein said living cells are insulin-producing cells.

29. The microcapsule of claim 28, wherein said insulin-producing cells are comprised in islets of Langerhans.

30. A pharmaceutical composition comprising a plurality of semi-permeable microcapsules as defined in claim 16, each of said microcapsules enclosing a material, and a pharmaceutically acceptable carrier.

31. The composition of claim 30, wherein said material is living cells.

32. The composition of claim 31, wherein said living cells are insulin-producing cells.

33. The composition of claim 32, wherein said insulin-producing cells are comprised in islets of Langerhans.

* * * * *